United States Patent [19]

Stoll et al.

[11] Patent Number: 5,266,714
[45] Date of Patent: Nov. 30, 1993

[54] PROCESS FOR THE PRODUCTION OF REACTION MIXTURES CONTAINING ESTER POLYOLS

[75] Inventors: Gerhard Stoll, Korschenbroich; Peter Daute, Essen; Rainer Hoefer, Duesseldorf; Roland Gruetzmacher, Wuelfrath; Hermann Kluth, Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 849,010

[22] PCT Filed: Oct. 13, 1990

[86] PCT No.: PCT/EP90/01737
§ 371 Date: Apr. 21, 1992
§ 102(e) Date: Apr. 21, 1992

[87] PCT Pub. No.: WO91/05759
PCT Pub. Date: May 2, 1991

[30] Foreign Application Priority Data
Oct. 21, 1989 [DE] Fed. Rep. of Germany ....... 3935127

[51] Int. Cl.$^5$ ............................................. C07C 51/00
[52] U.S. Cl. .................... 252/182.18; 554/116; 554/149; 252/182.25; 252/182.27
[58] Field of Search ................ 204/157; 554/149, 116; 549/553; 560/591, 594, 600, 601, 606

[56] References Cited

U.S. PATENT DOCUMENTS 3,125,592  3/1964  Nevin ................................. 554/116
4,118,405 10/1978  Hodakawski et al. ............. 554/122

Primary Examiner—José G. Dees
Assistant Examiner—Deborah D. Carr
Attorney, Agent, or Firm—Ernest G. Szoke; Wayne C. Jaeschke; Henry E. Millson, Jr.

[57] ABSTRACT

Process for the preparation of ester polyols by conducting the ring opening of epoxidized esters and/or alcohols with carboxylic acids by the controlled addition of the epoxidized compounds to the carboxylic acids wherein the carboxylic acids are present in at least stoichiometric quantities based on epoxide groups, to minimize unreacted epoxide groups and produce ester polyols having relatively low viscosities compared to those produced by the one-pot prior art process.

20 Claims, No Drawings

PROCESS FOR THE PRODUCTION OF REACTION MIXTURES CONTAINING ESTER POLYOLS

This invention relates to a process for the production of comparatively low-viscosity reaction mixtures containing ester polyols by reaction of epoxidized esters and/or alcohols with carboxylic acids.

The present invention also relates to the mixtures of ester polyols obtainable by the above process which predominantly contain ester polyols bearing free hydroxyl groups in the adjacent position to the ester group.

Polyols are important and versatile raw materials having a broad range of potential applications.

An inexpensive process for the production of polyols is based on the ring-opening reaction of polyepoxidized compounds with protic reactants.

The ring opening of epoxidized oils or fats with alcohols as proton donors is described, for example, in DE-PS 2 900 030, in EP-PS 113 798 and in U.S. Pat. Nos. 3,475,499 and 3,607,778.

The ring opening of epoxidized carboxylic acid esters with polyhydric alcohols is described in one embodiment of DE-OS 33 18 596. Specific reaction conditions are selected to suppress multiple reaction products which are formed by bridge formation of the free hydroxyl groups of the alkoxy radical of the hydroxylalkoxy carboxylic acids containing 2 or more fatty acid molecules. Thus, the epoxidized fatty acid derivative is added to a large excess of polyhydric alcohols, preferably in an excess of from 0.5 mol to more than 10 mol alcohol/mol epoxidized fatty acid derivative.

Acids are normally added as catalysts to accelerate the ring opening of epoxidized compounds with alcohols, but have to be removed after the reaction or remain in the polyol after neutralization with bases and can give rise to cloudy effects and shrinkage where the polyol is used in polyurethane compositions.

In the absence of catalysts, epoxidized oils or fats can be directly ring-opened with carboxylic acids, in which case reaction mixtures modified by hydroxy and acyloxy groups are formed.

The ring opening of soybean oil containing epoxide groups with acrylic acid or methacrylic acid is described, for example, in U.S. Pat. No. 4,016,059. The reaction is carried out by the so-called one-pot method, in which all the reactants are simultaneously reacted, and leads to a reaction mixture containing a hydroxy(meth)acryloxy soybean oil ester. The exact composition of the reaction mixture is determined inter alia by the quantity of acrylic acid used. Where acrylic acid is used in less than an equivalent quantity, based on the epoxide content of the soybean oil, residual contents of epoxide groups of up to 5.2% by weight can occur. Although the residual epoxide content can be reduced to 0.2% where an excess of acrylic acid is used, the reactions are always carried out in the presence of a solvent, such as ethyl benzene.

Comparable reactions of epoxidized soybean oil and acrylic acid inter alia in a molar ratio of 1:3 are described in U.S. Pat. No. 3,125,592, according to which reaction mixtures containing hydroxyacryloxy soybean oil esters are obtained as viscous liquids without solvents by the one-pot method.

Viscous liquids are also obtained in the reaction of epoxidized soybean oil with linseed oil fatty acid or dehydrated ricinoleic acid by the one-pot method (U.S. Pat. No. 2,909,537). Mixtures having undisclosed viscosities are apparently formed irrespective of the fatty acid used and the quantities in which it is used. However, the mixtures obtained contain unreacted linseed oil fatty acid or dehydrated ricinoleic acid which can cause problems, for example where they are subsequently used in polyurethane compositions.

The partial ring opening of epoxidized fats containing more than one epoxide group in the molecule with dicarboxylic acids, polycarboxylic acids or anhydrides thereof in substantially stoichiometric quantities is described in U.S. Pat. No. 3,180,749. In the process claimed in this document, the reaction which is carried out by the one-pot method is said to be terminated before the carboxylic acid has been completely consumed so that at least one unreacted epoxide group remains in each fatty acid molecule.

The ring-opening mixtures of epoxidized soybean oil with acids obtained by the one-pot method are mostly products of comparatively high viscosity which had to be diluted with solvents or heated before their use, for example as corrosion inhibitors (U.S. Pat. No. 2,909,537) or in polyurethane compositions (U.S. Pat. No. 4,016,059).

The problem addressed by the present invention was to produce comparatively low-viscosity reaction mixtures containing ester polyols by reaction of epoxidized compounds with carboxylic acids.

It has now surprisingly been found that comparatively low-viscosity reaction mixtures containing ester polyols can be obtained if the carboxylic acids are initially introduced in at least stoichiometric quantities and the epoxidized esters or alcohols are subsequently added with a time delay.

Accordingly, the present invention relates to a process for the production of reaction mixtures containing ester polyols by ring-opening reactions of epoxidized esters and/or alcohols with carboxylic acids, characterized in that, to obtain comparatively low-viscosity reaction products, the carboxylic acids are initially introduced in at least substantially stoichiometric quantities to the epoxide content of the reactant(s) and the epoxidized reaction component is subsequently introduced with such a time delay that substantial numbers of unreacted epoxide groups in the reaction mixture are avoided.

The present invention also relates to the mixtures of ester polyols obtainable by the above process which predominantly contain ester polyols bearing free hydroxyl groups in the adjacent position to the ester group.

The ester polyols in question are understood to be compounds which, on a statistical average, contain more than one free hydroxyl group per molecule and which at least partly contain an ester group in the adjacent position to the hydroxyl group.

In the production of the comparatively low-viscosity reaction mixtures containing ester polyols in accordance with the invention, the carboxylic acids are initially introduced and heated to temperatures above 80° C. and below 300° C. and preferably to temperatures above 100° C. and below 270° C. The choice of the reaction temperature is determined inter alia by the carboxylic acids initially introduced. Thus, reaction temperatures in the lower temperature range are applied where lower carboxylic acids are used whereas reaction temperatures in the higher temperature range are applied where higher carboxylic acids are used. Reaction temperatures above 300° C. lead to an increased percentage of condensed products and/or to decomposition of the reaction mixture, above all with relatively long reaction times.

According to the invention, the epoxidized esters and/or alcohols are subsequently added, preferably with intensive stirring, to the heated carboxylic acids initially introduced. According to the invention, the epoxidized reaction component is introduced with such a time delay that substantial numbers of unreacted epoxide groups in the reaction mixture are avoided. The contents of unreacted epoxide groups should be kept below 50% by weight. This figure of less than 50% by weight is the relative content of epoxide oxygen in the reaction mixture after complete addition of the epoxidized reactants and is based on the theoretically expected content of epoxide oxygen in the one-pot reaction, the values being corrected to allow for dilution by the carboxylic acid initially introduced. Distinctly lower contents than 50% by weight can be obtained by keeping the rate of introduction very low. For economic reasons, however, the rate of introduction should be as high as possible and should preferably not exceed 1.5 hours.

The higher the content of unreacted epoxide groups, the greater the probability that hydroxyl-functional ester polyols already present will open unreacted epoxide groups through the hydroxyl groups so that more highly condensed units will be formed. The content of unreacted epoxide groups can be determined by titration, for example by R. R. Jay's method (Analyt. Chemie 36 (1964), 667/8).

In one preferred embodiment, the time-delayed introduction of the epoxide compound is achieved by dropwise addition. However, any other controllable methods of addition may be used.

After the epoxidized reaction component has been added, the reaction mixture is left to react off at the reaction temperatures mentioned above until it has an absolute residual epoxide oxygen content of less than 1.0% by weight, preferably less than 0.5% by weight and, more preferably, less than 0.3% by weight.

According to the invention, any excess carboxylic acid is removed from the reaction mixture after the reaction. The excess carboxylic acid is preferably removed by distillation in vacuo, although it may also be removed by other methods, such as neutralization with a base and, optionally, subsequent filtration. Removal of the carboxylic acids by distillation in accordance with the invention requires different temperatures according to the carboxylic acid used and the vacuum applied, although these temperatures should not exceed the preferred reaction temperatures of up to 300° C.

According to the invention, epoxidized esters and/or epoxidized alcohols which, on a statistical average, contain more than one epoxide group and preferably two and more epoxide groups per molecule are used as the epoxidized reaction component for the preparation of reaction mixtures containing ester polyols.

The production of the epoxidized esters and/or alcohols is carried out completely or substantially completely by known methods, for example as described in EP 286 937 or DE-PS 1 042 565. According to the invention, the epoxidation of polyunsaturated esters and/or alcohols may even take place in part only, although in this case the epoxidized esters and/or epoxidized alcohols formed must contain more than one epoxide group per molecule on a statistical average.

Esters of epoxidized acids with alcohols and/or esters of epoxidized alcohols with acids may be used as the epoxidized esters. It is preferred to use epoxidized esters of monohydric to tetrahydric alcohols containing up to 40 carbon atoms, preferably up to 36 carbon atoms and, more preferably, from 1 to 22 carbon atoms, such as methanol, 2-ethyl hexanol, ethylene glycol, butanediol, neopentyl glycol, glycerol and/or pentaerythritol.

The epoxidized esters used preferably contain epoxidized acids containing up to 40 carbon atoms, preferably up to 36 carbon atoms and, more preferably, up to 22 carbon atoms. Suitable starting materials for epoxidized esters are the numerous animal and/or vegetable triglycerides, such as beef tallow, palm oil, lard, peanut oil, rapeseed oil, cottonseed oil, soybean oil, train oil, sunflower oil, coriander oil and/or linseed oil. Particularly preferred epoxidized esters are epoxidized soybean oil (epoxide oxygen content 5.8 to 6.5% by weight), epoxidized sunflower oil rich and/or poor in oleic acid (epoxide oxygen content 4.4 to 6.6% by weight), epoxidized linseed oil (epoxide oxygen content 8.2 to 8.6% by weight) and epoxidized train oil (epoxide oxygen content 6.3 to 6.7% by weight).

Preferred epoxidized alcohols are those containing 3 to 32 carbon atoms, preferably more than 12 carbon atoms and, more preferably, up to 22 carbon atoms. Particularly preferred epoxidized alcohols are those containing more than one and preferably two and/or three epoxide groups per molecule and/or mixtures of epoxidized alcohols containing more than one epoxide group per molecule on a statistical average. Under the conditions mentioned, it is possible for example to use epoxy derivatives of the alcohols 10-undecen-1-ol, 9c-octadecen-1-ol (oleyl alcohol), 9t-octadecen-1-ol (elaidyl alcohol), 9c-octadecen-1,12-diol (ricinoleic alcohol), 9c,12c-octadecadien-1-ol (linoleyl alcohol), 9c,12c,15c-octadecatrien-1-ol (linolenyl alcohol), 9c-eicosen-1-ol (gadoleyl alcohol), 13c-docosen-1-ol (erucic alcohol) and/or 13t-docosen-1-ol (brassidyl alcohol). Mixtures of epoxidized alcohols and epoxidized esters in any ratio may also be used as the epoxidized reaction component.

In the process according to the invention, the epoxidized reaction components mentioned are ring-opened completely or substantially completely with carboxylic acids. Monobasic carboxylic acids are particularly suitable for this purpose. Suitable carboxylic acids are synthetic, natural, aliphatic, aromatic, branched and/or unbranched carboxylic acids containing up to 40 carbon atoms, preferably up to 30 carbon atoms and, more preferably, up to 22 carbon atoms. Saturated and unsaturated carboxylic acids and mixtures thereof are suitable for ring-opening. In a particularly preferred embodiment, formic acid, acetic acid, propionic acid, caprylic acid, capric acid, behenic acid, palmitoleic acid, oleic acid, linolenic acid and/or linolenic acid is/are initially introduced as the carboxylic acid. Relatively high percentages of unsaturated carboxylic acids give particularly low-viscosity reaction mixtures containing ester polyols.

According to the invention, the epoxidized reaction components are introduced with time delay in quantities of up to 1:10, preferably in at most equimolar quantities and, more particularly, in slightly less than the equimolar quantity—expressed as mol-% epoxide and based on mol-% acid group—relative to the carboxylic acids initially introduced.

In the preferred embodiment of the invention, preferably more than 1 and less than 1.5 acid molecules and, more particularly, more than 1 and less than 1.1 acid molecules per epoxide group of the epoxidized reactant are initially introduced.

The reaction mixtures containing ester polyols obtained by the process according to the invention are light yellow to light brown liquids of comparatively low viscosity.

Preferably up to 50% and, more preferably, between 10 and 40% of the reaction mixtures produced in accordance with the invention have lower viscosities, as measured in mPa.s at 20° C. in accordance with DIN 53 015 (Höppler), than those produced by the one-pot method.

The absolute viscosity values of the reaction mixtures produced in accordance with the invention are dependent to a large extent on the molecular weight and the chemical constitution of the epoxidized reactants and the carboxylic acids initially introduced. The reaction mixtures produced in one particular embodiment by ring-opening of epoxidized fats and/or oils with oleic acid have viscosities of well below 2,000 mPa.s and, more particularly, below 1,500 mPa.s. Reaction products of epoxidized fats and/or oils with unsaturated fatty acids, such as linoleic and linolenic acid, or fatty acid mixtures, such as linseed oil fatty acid, will have comparable viscosities.

On a statistical average, the ester polyol mixtures obtained by the process according to the invention contain more than 1 and preferably more than 1.5 free hydroxyl groups per molecule. The mixtures of ester polyols contain ester groups in the adjacent position to the hydroxyl group where the epoxides have been ring-opened by the carboxylic acid initially introduced. The rest of the mixture contains dimeric, trimeric and/or higher condensates through ring-opening of the epoxides with ester polyols already present. It can be shown by gel permeation chromatography (GPC) (standard (poly)styrene) that the ester polyol mixtures produced by the one-pot method have a relatively high percentage content of higher condensates.

It is possible by the process according to the invention to produce products predominantly containing non-condensed ester polyols which, on a statistical average, preferably contain more than one free hydroxyl group and an ester group adjacent thereto.

The mixtures obtainable by the process according to the invention contain monomeric ester polyols containing ester groups adjacent the free hydroxyl group of synthetic, natural, aliphatic, aromatic, branched and/or unbranched carboxylic acids containing up to 40 carbon atoms and, more particularly, between 8 and 22 carbon atoms. Equal preference is attributed to saturated and unsaturated carboxylic acids, more particularly caprylic, capric, oleic, linoleic and/or linolenic acid.

The production of the reaction mixtures containing ester polyols in accordance with the invention is described in the following Examples. The characteristic data of the ester polyol mixtures thus produced, such as their hydroxyl value, acid value, residual epoxide content, Höppler viscosity at 20° C., etc., are set out in Table 1 where they are compared with those of ester polyol mixtures produced by the one-pot method.

EXAMPLE 1

823 g technical oleic acid (AV 200.5, IV 94), corresponding to 2.9 mol based on acid value, were heated with stirring to 160° C. in a reaction vessel. 661 g soybean oil epoxide (epoxide oxygen content 6.78% by weight), corresponding to 2.8 mol based on epoxide content, were then added with stirring with such a time delay (75 minutes) that the absolute content of unreacted epoxide groups in the reaction mixture did not exceed 1.44% by weight. After the addition, the reaction mixture was kept at 160° C. until the residual epoxide oxygen content had fallen below 0.3% by weight (3 hours). The unreacted oleic acid (96 g) was distilled off in a vacuum (below 10 Pas) up to 200° C. The polyol mixture was obtained in the form of a clear dark yellow liquid having the following characteristic data: OHV 40.7, SV 194, IV 54.7, AV 6.5.

EXAMPLE 2

1225 g head-fractionated fatty acid (60% $C_8$, 35% $C_{10}$, AV 361.9), corresponding to 7.9 mol based on acid value, were introduced into a reaction vessel and heated with stirring to 150° C. 1770 g soybean oil epoxide (epoxide oxygen content 6.78% by weight), corresponding to 7.5 mol based on epoxide content, were then added with stirring with such a time delay (60 minutes) that the absolute content of unreacted epoxide groups in the reaction mixture did not exceed 1.6% by weight. After the addition, the reaction temperature was slowly increased to 170° C. and the reaction mixture was kept at that temperature until the residual epoxide oxygen content had fallen below 0.15% by weight (2 hours). The unreacted head-fractionated fatty acid (470 g) was distilled off in vacuo (below 10 Pas) up to 200° C. The polyol mixture was obtained in the form of a clear yellow liquid having the following characteristic data: OHV 96, SV 235, AV 1.5.

EXAMPLE 3

948 g technical monomer fatty acid (a product mixture obtained in accordance with M.J.A.M. den Otter (Fette Seifen, Anstrichmittel 8/1970, 667–673), AV 174, IV 70.1), corresponding to 3.9 mol based on acid value, were heated with stirring to 160° C. in a reaction vessel. 661 g soybean oil epoxide (epoxide oxygen content 6.78% by weight), corresponding to 2.8 mol based on epoxide content, were then added with stirring with such a time delay (60 minutes) that the absolute content of unreacted epoxide groups in the reaction mixture did not exceed 1.33% by weight. After the addition, the reaction mixture was kept at 160° C. until the residual epoxide oxygen content had fallen below 0.28% by weight (3 hours). The unreacted technical monomer fatty acid (164 g) was distilled off in vacuo (below 10 Pas) up to 270° C. The ester polyol mixture was obtained in the form of a clear dark yellow liquid having the following characteristic data: OHV 40.1, SV 190.9, IV 37.9, AV 8.5.

EXAMPLE 4

234 g propionic acid, corresponding to 3.15 mol based on the acid value, were heated with stirring to 140° C. in a reaction vessel. 713 g soybean oil epoxide (epoxide oxygen content 6.73% by weight), corresponding to 3.0 mol based on the epoxide content, were then added while stirring with such a time delay (83 minutes) that the absolute content of unreacted epoxide groups in the reaction mixture did not exceed 1.67% by weight. After the addition, the reaction mixture was kept at 140° C. until the residual epoxide oxygen content had fallen below 0.18% by weight (5 hours). The unreacted propionic acid (114 g) was distilled off in vacuo (below 10 Pas) up to 190° C. The ester polyol mixture was obtained in the form of a clear dark yellow liquid having the following characteristic data: OHV 129, SV 277.5, IV 4.3, AV 2.1.

EXAMPLE 5

631 g head-fractionated fatty acid (60% $C_8$, 35% $C_{10}$, AV 358) were introduced into a reaction vessel and heated with stirring to 150° C. 1043 g rapeseed oil epoxide low in erucic acid (epoxide oxygen content 5.95% by weight) were then added while stirring with such a time delay (60 minutes) that the absolute content of unreacted epoxide groups in the reaction mixture did not exceed 1.6% by weight. After the addition, the reaction mixture was slowly increased to 170° C. and the reaction mixture was kept at that temperature until the residual epoxide oxygen content had fallen below 0.17% by weight (3 hours). The unreacted head-fractionated fatty acid (201 g) was distilled off in a vacuum (below 10 Pas) up to 200° C. The polyol mixture was obtained in the form of a clear yellow liquid having the following characteristic data: OHV 119, SV 237, AV 3.1, and a viscosity of 6238 mPa.s (Höppler, 20° C.).

EXAMPLE 6

490 g head-fractionated fatty acid (60% $C_8$, 35% $C_{10}$, AV 361.9) were introduced into a reaction vessel and heated with stirring to 160° C. 716 g soybean oil epoxide (epoxide oxygen content 6.78% by weight) were then added with stirring with such a time delay (6.5 hours) that the absolute content of unreacted epoxide groups in the reaction mixture did not exceed 1.6% by weight. After the addition, the reaction temperature was slowly increased to 170° C. and the reaction mixture was kept at that temperature until the residual epoxide oxygen content had fallen below 0.17% by weight (1 hour). The unreacted head-fractionated fatty acid (71 g) was distilled off in a vacuum (below 10 Pas) up to 200° C. The polyol mixture was obtained in the form of a clear yellow liquid having the following characteristic data: OHV 99, IV 3.7, SV 239, AV 3.9, and a viscosity of 4160 mPa.s (Höppler, 20° C.).

COMPARISON EXAMPLE 1

819 g technical oleic acid (AV 201.5), corresponding to 2.9 mol based on the acid value, were heated with stirring to 160.C together with 666 g soybean oil epoxide (epoxide oxygen content 6.73% by weight), corresponding to 2.8 mol based on the epoxide content, and the reaction mixture was kept at that temperature until the residual epoxide oxygen content had fallen below 0.18% by weight (4 hours). The unreacted oleic acid was distilled off in vacuo (below 10 Pas) up to 260° C. The ester polyol mixture was obtained in the form of a clear dark yellow liquid having the following characteristic data: OHV 51, SV 192, IV 50.4, AV 2.3.

COMPARISON EXAMPLE 2

234 g propionic acid, corresponding to 3.15 mol based on the acid value, were heated with stirring to 140° C. together with 713 g soybean oil epoxide (epoxide oxygen content 6.73% by weight), corresponding to 3.0 mol based on the epoxide content, and the reaction mixture was kept at that temperature until the residual epoxide oxygen content had fallen below 0.21% by weight (5 hours). The unreacted propionic acid (115 g) was distilled off in a vacuum (below 10 Pas) up to 185° C. The ester polyol mixture was obtained in the form of a clear dark yellow liquid having the following characteristic data: OHV 126, SV 273.8, IV 1.8, AV 1.8.

COMPARISON EXAMPLE 3

1234 g head-fractionated fatty acid (60% $C_8$, 35% $C_{10}$, AV 358), corresponding to 7.9 mol based on the acid value, were heated with stirring to 140° C. together with 1762 g soybean oil epoxide (epoxide oxygen content 6.81% by weight), corresponding to 7.5 mol based on the epoxide content, after which the temperature was slowly increased to 170° C. The reaction mixture was kept at that temperature until the residual epoxide oxygen content had fallen below 0.12% by weight (3 hours). The unreacted head-fractionated fatty acid (453 g) was distilled off in a vacuum (below 10 Pas) up to 185° C. The ester polyol mixture was obtained in the form of a clear dark yellow liquid having the following characteristic data: OHV 102.7, IV 3.6, AV 5.0.

TABLE 1

|   | Hydroxyl value (OHV) | Saponification value (SV) mg/KOH | Iodine value (IV) | Acid value (AV) | Residual epoxide content in % | Viscosity in mPa · s |
| --- | --- | --- | --- | --- | --- | --- |
| Ex. 1 Oleic acid | 40.7 | 194.0 | 54.7 | 6.5 | <0.30 | 1360 |
| Ex. 2 H.-f. fatty acid | 96.0 | 235.0 | — | 1.5 | <0.15 | 4750 |
| Ex. 4 Propionic acid | 129.0 | 277.5 | 4.3 | 2.1 | <0.18 | 15050 |
| Comp. Ex. 1 Oleic acid | 51.0 | 192.0 | 50.4 | 2.3 | <0.18 | 1936 |
| Comp. Ex. 2 Propionic acid | 126.0 | 273.8 | 4.5 | 1.8 | <0.21 | 24850 |
| Comp. Ex. 3 H.-f. fatty acid | 102.7 | 236.8 | 3.6 | 5.0 | <0.21 | 7543 |

We claim:
1. A process for the preparation of an ester polyol or a mixture of ester polyols comprising the steps of
(A) adding to at least one carboxylic acid maintained at a temperature above 80° C. but below 300° C. at least one epoxidized compound selected from the group consisting of epoxidized esters and epoxidized alcohols wherein the carboxylic acid is present in at least about stoichiometric quantity based on the epoxide content of the epoxidized compound, and the epoxidized compound is added to the carboxylic acid, to ring open the epoxide groups, at a controlled rate of addition such that less than 50% by weight of the theoretically possible quantity of epoxide oxygen is present in the reaction mixture after complete addition of the at least one epoxidized compound; and (B) isolating an ester polyol or mixture of ester polyols from said reaction mixture.

2. The process of claim 1 wherein in step A said temperature is from above 100° C. to below 270° C.

3. The process of claim 1 wherein in step A the at least one epoxidized compound is added dropwise to the stirred reaction mixture.

4. The process of claim 1 wherein the at least one epoxidized compound is added to the at least one carboxylic acid in a quantity ranging from slightly less than equimolar to a molar ratio of about 1:10, expressed as mol % epoxide groups based on mol % carboxylic acid groups.

5. The process of claim 4 wherein said quantity is about equimolar.

6. The process of claim 1 wherein the step A following the controlled addition of the at least one epoxidized compound, heating is continued until the reaction mixture has an absolute residual epoxide oxygen content of less than about 1% by weight.

7. The process of claim 6 wherein heating is continued until the reaction mixture has an absolute residual epoxide oxygen content of less than about 0.5% by weight.

8. The process of claim 6 wherein heating is continued until the reaction mixture has an absolute residual epoxide oxygen content of less than about 0.3% by weight.

9. The process of claim 6 wherein in step B unreacted carboxylic acid is removed from the reaction mixture.

10. The process of claim 9 wherein the unreacted carboxylic acid is removed from the reaction mixture by distillation in vacuo.

11. The process of claim 1 wherein the at least one carboxylic acid is at least one monobasic carboxylic acid.

12. The process of claim 1 wherein the at least one monobasic carboxylic acid is selected from the group consisting of aromatic and saturated and unsaturated branched and unbranched aliphatic carboxylic acids containing up to 40 carbon atoms.

13. The process of claim 12 wherein the at least one monobasic carboxylic acid is a saturated aliphatic carboxylic acid, an unsaturated aliphatic carboxylic acid, or a mixture of two or more such acids, containing up to 36 carbon atoms.

14. The process of claim 1 wherein in step A the epoxidized compound is a mixture of epoxidized esters containing an average of more than one epoxide group per molecule.

15. The process of claim 14 wherein the expoxidized esters are esters of monohydric, dihydric, trihydric, or tetrahydric alcohols.

16. The process of claim 14 wherein the epoxidized esters are esters of epoxidized carboxylic acids.

17. The process of claim 1 wherein in step A the epoxidized compound is at least one epoxidized alcohol containing from 3 to 32 carbon atoms.

18. A mixture of ester polyols produced by the process of claim 1 which contain predominantly ester polyols having free hydroxyl groups in the position adjacent to the position of the ester groups formed from the ring-opening of the epoxide groups.

19. The mixture of ester polyols of claim 18 wherein the ester polyols contain ester groups of $C_1$–$C_{40}$ monobasic carboxylic acids.

20. The process of claim 1 wherein following step A and prior to step B the reaction is continued until an absolute residual epoxide oxygen content of less than 1% by weight is obtained in the reaction mixture.

* * * * *